(12) United States Patent
Natunen (10) Patent No.: US 6,878,819 B1
(45) Date of Patent: Apr. 12, 2005

(54) FUCOSYLATED OLIGOSACCHARIDES AND PROCESS FOR THEIR PREPARATION

(76) Inventor: Jari Natunen, Meritullinkatu 6 C 18, FIX-00170 Helsinki (FI)

( * ) Notice: Subject to any disclaimer, the term of this patent is extended or adjusted under 35 U.S.C. 154(b) by 0 days.

(21) Appl. No.: 10/089,229

(22) PCT Filed: Sep. 21, 2000

(86) PCT No.: PCT/FI00/00803

§ 371 (c)(1), (2), (4) Date: Jul. 18, 2002

(87) PCT Pub. No.: WO01/23398

PCT Pub. Date: Apr. 5, 2001

(30) Foreign Application Priority Data

Sep. 28, 1999 (FI) .............................................. 19992070

(51) Int. Cl.$^7$ .......................... C08B 37/00; C07H 15/12; C07H 5/04
(52) U.S. Cl. ..................... 536/53; 536/18.7; 536/123.1; 536/55.1; 536/55.3; 536/124; 514/54
(58) Field of Search ..................... 536/53, 18.7, 123.1, 536/55.1, 55.3, 124, 54; 514/54

(56) References Cited

U.S. PATENT DOCUMENTS

| 5,374,655 A | 12/1994 | Kashem et al. |
| 5,759,823 A | 6/1998 | Wong et al. |
| 5,922,577 A | 7/1999 | Defree et al. |
| 6,077,695 A | * 6/2000 | Nilsson et al. |
| 6,319,695 B1 | * 11/2001 | Wong et al. |

FOREIGN PATENT DOCUMENTS

EP    0 919 563 A2    6/1999

OTHER PUBLICATIONS

Qian et al., J. Am. Chem. Soc., vol. 120, pp. 2184–2185 (1998).
Nimtz et al., Glycoconjugate Journal, vol. 15, pp. 873–883 (1998).
Probert et al., Tetrahedron Letters, vol. 38, No. 33, pp. 5861–5864 (1997).

* cited by examiner

Primary Examiner—James O. Wilson
Assistant Examiner—Michael C. Henry
(74) Attorney, Agent, or Firm—Birch, Stewart, Kolasch & Birch, LLP (57) ABSTRACT

The present invention relates to a process for the preparation of oligosaccharides or oligosaccharide containing compounds, especially N-acetyl-chitooligosaccharides having a fucosylated monosaccharide. The invention also relates to novel oligosaccharides or oligosaccharide containing compounds, especially N-acetyl-chitooligosaccharides, which are fucosylated and optionally covalently bound to a carrier molecule.

27 Claims, 5 Drawing Sheets

FUCOSYLATED OLIGOSACCHARIDES AND PROCESS FOR THEIR PREPARATION

This application is the national phase under 35 U.S.C. §371 of PCT International Application No. PCT/FI00/00803 which has an International filing date of Sep. 21, 2000, which designated the United States of America.

FIELD OF INVENTION

The present invention relates to novel fucosylated oligosaccharides or oligosaccharide containing compounds which are analogues to natural oligosaccharides and which contain at least one fucosylated monosaccharide unit. The invention also relates to a process for the preparation of such oligosaccharides or oligosaccharide containing compounds.

BACKGROUND OF THE INVENTION

Fucosylated mammalian glycans have functions in fertilization (1), early differentiation of embryo (2), brain development (3,4), and leukocyte extravasation (5,6). the α1–3/4fucosylated oligo- and polysaccharides being conjugated to lipids and proteins or as free oligosaccharides such as the oligosaccharides of human milk. The fucosylated N-acetyllactosamines (Lewis x, Galβ1–4(Fucα1–3)GlcNAc and Lewis a, Galβ1–3(Fucα1–4)GlcNAc) and fucosylated N-acetyllactosdiamine (LexNAc, GalNAcβ1–4(Fucα1–3)GlcNAc) occur often as terminal sequences such as Galβ1–4(Fucα1–3)GlcNAcβ1–2Manα-, Galβ1–3)(Fucα1–4)GlcNAcβ1–2Manα-, GalNAcβ1–4(Fucα1–3 (GlcNAcβ1–2Manα-, Galβ1–4(Fucα1–3)GlcNAcβ1–3 (Galβ-/GalNAcα-, Galβ1–3(Fucα1–4)GlcNAcβ1–3Galβ-, Galβ1–4(Fucα1–3) GlcNAcβ1–4Manα-, Galβ1–3 (Fucα1–4(GlcNAcβ1–4Manα-, and Galβ1–4(Fucα1–3) GlcNAcβ1–6Galβ-/GalNAcα-/Manα-. In the middle of lactosamine-type chains the Lewis x-sequences, -GlcNAcβ1–3Galβ1–4(Fucα1–3)GlcNAcβ1–3Gal are common, but also Lewis a-structures, Galβ1–3(Fucα1–4) GlcNAc, are present with a possibility for repeating the sequence chain. In the free oligosaccharides found mainly in human milk, the α1–3fucosylated epitope at the reducing end of the saccharide is commonly lactose (Galβ1–4Glc) or its elongated/substituted form such as Galβ1–4(Fucα1–3) Glc, Fucα1–2Galβ1–4(Fucα1–3)Glc, Galβ1–4GlcNAcβ1–3Galβ1–4(Fucα1–3)Glc, Galβ1–3GlcNAcβ1–3Galβ1–4(Fucα1–3(Glc, and Galβ1–4 (Fucα1–3)GlcNAcβ1–3Galβ1–4(Fucα1–3)Glc. Analogs of these could be useful for studies of specificities of biological activities of the natural mammalian α1–3/4fucosylated sequences.

The fucosylation step in the biosynthesis of these glycans is accomplished by the family of α1–3/4fucosyltransferases (Fuc-Ts). In man, at least Fuc-Ts III–VII and IX are expressed (7–9), and enzymatically active homologs are known in other animals and bacteria.

α1–3Fucosyltransferases transfer fucose to position 3 of GlcNAc or Glc residues in Galβ1–4GlcNAc (LacNAc), GalNAcβ1–4GlcNAc (LacdiNAc) and Galβ1–4Glc (lactose) to synthesize the bioactive epitopes Galβ1–4 (Fucα1–3)GlcNAc (Lewis x, Lex), GalNAcβ1–4(Fucα1–3) GlcNAc (LexNAc), and Galβ1–4(Fucα1–3)Glc, respectively. All human Fuc-Ts are known to use Galβ1–4GlcNAc-type acceptors (7,9). GalNAcβ1–4GlcNAc serves also as an acceptor for the Fuc-Ts of human milk (10). Human Fuc-Ts III and V have also α1–4fucosyltransferase activity using acceptors such as Galβ1–3GlcNAc (type I N-acetyllactosamine) to synthesize Galβ1–3(Fucα1–4)GlcNAc (Lewis a). At least human Fuc-Ts III and V and (weakly VI) are able to fucosylate lactose and related oligosaccharides to structures containing Galβ1–4(Fucα1–3)Glc sequences.

Enzymatic α1–3fucosylation of N-acetyl-chitobiose has been described, se U.S. Pat. No. 5,759,823, but the product was not characterized. The reducing N-acetyl-chitobiose contains also the epimer in which there is ManNAc at the reducing end, and it is not known from the data of the said U.S. patent if N-acetyl-chitobiose or its reducing-end epimer was fucosylated. Saccharides with fucosylated reducing-end GlcNAc are not considered useful as they are labile and degrade even in aqueous solutions at near neutral pH. The reducing-end fucosylated GlcNAc is very rate, or non-existent, in mammalian natural oligosaccharides, possibly because of the lability which could make it useless also in vivo for biological functions.

The present invention describes saccharide epitope analogues of the mammalian fucosylated saccharide chains, as well as their synthesis. An effective method to synthesize such epitopes is to use α1–3 fucosyltransferases or α1–3/4fucosyltransferases for fucosylation of novel acceptor sequences. Some of the acceptor sequences can be synthesized from cheap natural polysaccharides such as cellulose, chitin, chondroitin/chondroitin sulphates, or hyaluronic acid, also natural polysaccharides with the sequence Glcβ1–(3Glcβ1–4Glcβ1-)$_n$3Glc could be used to synthesize acceptors. β1–4GlcNAc transferase and UDP-GlcNAc can be used to generate GlcNAcβ1–4GlcNAcβ1- linked to Gal, GlcNAc or Man (11) and these can be used to make other analogues. Certain parasites have also been reported to contain N-acetyl-chitooligosaccharides which could be used as acceptors for the fucosylation reaction (12).

Interestingly the novel fucosylations of N-acetyl-chitooligosaccharides (N-acetyl-chitotriose and larger) described here occured to the non-reducing subterminal residue (forming a terminal Lewis x-like structure with a linkage structure similar to human glycans) and not to the reducing-end GlcNAc as in plant N-glycans.

SUMMARY OF THE INVENTION

In a first aspect, the present invention is directed to novel fucosylated oligosaccharides and oligosaccharide type compounds, especially N-acetyl-chitooligosaccharides which are α1–3 fucosylated in the monosaccharide at the position subterminal to the non-reducing end of the oligosaccharide. The present invention is also directed to a process for the preparation of such compounds, which results in a site-specific fucosylation by the use of α1–3fucosyltransferase or α1–3/4fucosyltransferase enzyme to glycosylate the oligosaccharide acceptor substrate with L-fucose.

DESCRIPTION OF THE DRAWINGS

In the drawing,

FIG. 1(A) is a HPAE-chromatography of the neutral Fuc-TV fucosylation products of N-acetyl-chitotetraose. Fucosylated product (Glycan 4, FGN$_4$; for structures of Glycans 3–7, see Table 1) eluted at 7.62 min and the putative acceptor at 9.74 min. in the isocratic run with 40 mM NaOH. (B) shows HPAE-chromatographic purification of fucosylated N-acetyl-chitohexaose (FGN$_6$) eluting at 7.09 min., putative N-acetyl-chitohexaose peak at 9.04 min in the isocratic run with 40 mM NaOH. The saccharides were from Fuc-TV reaction.

DETAILED DESCRIPTION OF THE INVENTION

Specifically the present invention concerns fucosylated oligosaccharide compounds having the formula In the formula I, A is H or a glycosidically β1–3 linked D-glucopyranosyl residue (Glcβ1–3), $R_1$ is OH, $R_2$ is H and $R_3$ is OH or acylamido, —NH-acyl (i.e. monosaccharide 1 is Glc, or GlcNAcyl) or $R_1$ is H, $R_2$ is OH and $R_3$ is acetamido —NHCOCH$_3$ (i.e. monosaccharide 1 is GlcNAc), B is H, or an α-L-fucosyl or an α-L-fucosyl analogue, and $R_4$ is OH or acetamido —NHCOCH$_3$ (i.e. monosaccharide 2 is optionally fucosylated Glc or GlcNAc), the curved line between the saccharide units indicating that the monosaccharide 1 is β1–4 linked to monosaccharide 2 when B is linked to the position 3 of the monosaccharide 2, and the monosaccharide 1 is β1–3 linked to monosaccharide 2 when B is linked to the position 4 of the monosaccharide 2, monosaccharide 1 is GlcNAc only when monosaccharide 2 is Glc, n is 1 to 100, with the proviso that there is always at least one α-fucosyl or α-fucosyl analogous group present in the molecule, and i) p and k are 0 and m is 1, in which case X is H, an aglycon residue or a monosaccharide selected from the group consisting of Glc, GlcNAc, Gal or GlcNAc, optionally in reduced form, or oligosaccharide containing one or more of said monosaccharide units, the monosaccharide 2 being β1–2, β1–3, β1–4 or β1–6 linked to saccharide X, with the proviso that X is not H when both monosaccharides 1 and 2 are GlcNAc, B is L-fucosyl and n is 1, or ii) p is 1, k is 0 or 1 and $1 \leq m \leq 1000$, in which case X is a straight bond, or a mono- or oligosaccharide as defined under i), Y is a spacer or linking group capable of linking the saccharide 2 or X to Z, and Z is a mono- or polyvalent carrier molecule.

In the above formula, as well as below, Glc means a D-glucose residue and Gal means a D-galactose residue. Fuc or F means a L-fucose residue. GlcNAc or GN means a N-acetyl-D-glucose amine residue. The monosaccharides are in pyranose form when glycosidically linked.

B as an analogue to the L-fucosyl residue is preferably a compound that contains a hydroxy-methyl group in place of the methyl group in 6 position of fucosyl, that is L-galactosyl, or a deoxy derivative of L-fucosyl, or an analogue where a di- to tetrasaccharide is linked to C6. Most preferably, however, B is H or L-fucosyl.

$R_3$ as an acylamido group is preferably an alkanoylamido group with 2 to 24 carbon atoms and 0 to 3 double bonds between carbon atoms in a straight chain. Preferably $R_3$ is acetamido —NH—COCH$_3$, or an alkanoylamido group with 8 to 24 carbon atoms, and 1 to 3 double bonds. m is preferably 1 to 100 and most preferably 1 to 10, and n is preferably 1 to 10.

An oligosaccharide in the meaning of X contains preferably from 2 to 10 monosaccharide units, the monosaccharide units preferably being glycosidically β1–4 or β1–3 linked Glc or GlcNAc residues.

An aglycon group is preferably a hydrocarbon group, such as a $C_{1-20}$ alkyl or $C_{2-20}$ alkenyl group, a $C_{3-10}$ cycloalkyl or cycloalkenyl group, or aryl or aralkyl group containing up to 10 carbon atoms in the aromatic ring, alkyl having the meaning given above, for example a phenyl group or benzyl group, or a heterocyclic group, that is a cycloalkyl or an aryl group as defined containing one or more heteroatoms O, S or N in the ring(s).

A preferred aglycon group is a lower alkyl or alkenyl group of 1 to 7, or 2 to 7 carbon atoms, respectively, or a phenyl or benzyl group. A preferred heterocyclic aglycon group is 4-methylumbelliferyl.

The spacer group Y, if present, can be any group that is capable of linking the group X or saccharide 2 to the carrier molecule Z, and such groups and methods of linking are known in the art, and also commercially available. For example when X is a saccharide, a bond between X and Y can be formed by reacting an aldehyde or a carboxylic acid with X at its $C_1$ or by introducing any aldehyde or carboxylic acid group in X through oxidation, to form a suitable bond such as —NH—, —N(R)— where R is an alkyl group, or a hydroxyalkylamine, an amide, an ester, a thioester or thioamide. A suitable bond is also —O— or —S—, see e.g. Stowell et al Advances in Carbohydrate Chemistry and Biochemistry, 37 (1980), 225-.

Thus the present invention provides fucosylated oligosaccharide compounds as such or covalently bound to a carrier molecule. The carrier molecule can be mono- or polyvalent, and is preferably selected from polymers, such as polyacrylamides, polyols, polysaccharides, such as agarose, bimolecules, including peptides and proteins, bovine or human serum albumin being commonly used carriers for example in immunoassays.

A preferred group of compounds with the formula I comprises the following wherein the symbols have the meanings given in connection with the formula I above. In the above formula, the monosaccharides 1 and 2 are preferably independently Glc and GlcNAc, B is L-fucosyl, and X is Glc or GlcNAc or a β1–3 or β1–4 linked oligomer comprising up to 10 units of Glc and/or GlcNAc. When p and k=0 and m=1, the compounds have the formula

IB

Monosaccharide residue 1        Monosaccharide residue 2 wherein the symbols have the same meanings as given above in the formula IA, or X can also be H provided the monosaccharides 1 and 2 are both Glc.

The compounds of the formula IA and IB are thus oligosaccharides that are fucosylated in the subterminal or penultimate non-reducing end monosaccharide. According to the invention it has been discovered that this specific fucosylation results in highly stable oligosaccharides, especially N-acetyl-chitooligosaccharides. According to a further preferred embodiment of the invention, the saccharides have the formula Glc/GlcNAcβ1–4(Fucβ1–3)Glc/GlcNAc(β1–4Glc/GlcNAc)$_{n'}$.

In the above formula, n' is the integer 1 to 8, preferably 1 to 6.

According to another embodiment of the invention, the saccharides have the formula GlcNAcylβ1–4(Fucα1–3)GlcNAc(β1–4GlcNAc)$_{n'}$.

wherein n' has the meaning give above and acyl is an alkanoyl group which preferably contains 8 to 24 carbon atoms and 1 to 3 double bonds. Preferably 1<n'<6, more preferably 2<n'<4.

According to the invention the compounds of the formula I are prepared by fucosylating a compound of the formula I wherein B is always H, with a donor nucleotide sugar containing L-fucose, or an analogue thereof, in the presence of a fucosyltransferase enzyme, and optionally recovering the fucosylated saccharide so prepared. Such a reaction may be carried out on the starting oligosaccharide prior to the optional binding the oligosaccharide to the carrier molecule Y. In the alternative, it is also possible to fucosylate a carrier bound oligosaccharide. Such a reaction is carried out essentially in the same manner as with non-bound oligosaccharides. For example, a N-acetyl-chitooligosaccharide such as a N-acetyl-chitotriose, can be linked to bovine serum albumin BSA through a spacer or it can be reductively aminated in a known manner to BSA, the reduced residue forming the spacer. In the fucosylation reaction, preferably an excess GDP-Fuc and a lower concentration of acceptor sites (0.1–1 mM) are used. If BSA is the carrier, the reaction buffer contains no non-glycosylated BSA. The products can be purified by methods of protein chemistry and the level of fucosylation can be checked by MALDI-TOF mass spectrometry, as described in more detail below. The fucosylation can be repeated if the reaction is incomplete.

Oligosaccharides with an aglycon group as X can be fucosylated essentially as has been described, preferably using lower acceptor concentrations (0.1–1 mM). The products can be purified using chromatographic methods including gel filtration and with partial reaction cleavage with N-acetylhexosaminidase from jack beans. As an example, one obtains GlcNAcβ1–4(Fucα1–3)GlcNAcβ1-benzyl from GlcNAcβ1–4GlcNAcβ1-benzyl, GlcNAcβ1–4(Fucα1–3)GlcNAcβ1-O-methyl from GlcNAcβ1–4GlcNAcβ1-O-methyl, and GlcNAcβ1–4(Fucα1–3)GlcNAcβ1–4GlcNAcβ1-O-4-methylumbelliferyl from GlcNAcβ1–4GlcNAcβ1–4GlcNAcβ1-O-4-methylumbelliferyl.

According to a preferred embodiment of the invention, the fucosyltransferase is human α1–3-fucosyltransferase or human α1–3/4fucosyltransferase, especially one of human fucosyltransferases III–VII, IX, or α1–3/4fucosyl transferase of human milk. According to another preferred embodiment, the L-fucose is in the form of GDP-L-fucose.

According to an embodiment for making the preferred compounds described above, the starting oligosaccharide contains 3 to 10, especially 3 to 8 β1–4 saccharide units. Such units are preferably N-acetyl-D-glucosamine residues, GlcNAc, the corresponding starting materials thus being N-acetyl-chitooligomers with formula (GlcNAcβ1–4)$_{3-10(8)}$. According to a second preferred embodiment, the oligosaccharides contain 2 to 10, especially 2 to 6 β1–4 D-glucose units, Glc, the corresponding starting materials thus being cellooligomers with formula (Glcβ1–4)$_{2-10(8)}$.

According to the invention it is also possible to include a further step of reacting the protect obtained with a β-N-acetyl-hexosaminidase under sufficiently strong conditions and in an amount sufficient to release the non-reducing terminal monosaccharide. It is also possible to react the product obtained with a β-N-acetyl-hexosaminidase under less severe conditions in order to release a monosaccharide from its reducing terminal. In this manner, a product is obtained which contains one saccharide unit less than the primary oligosaccharide product. This latter reaction may also be controlled in such a manner that the enzyme primarily degrades any remaining non-fucosylated substrate. This method thus provides a convenient way of purifying the reaction mixture after the fucosylating step.

Due to the fucose unit, the novel oligosaccharides are stable compounds and as such useful in a number of applications. As such they can, for example, be used as substrates for testing, identifying and differentiating enzymes, such as chitinases, and when bound to a support they find use in immunoassays and affinity chromatography. They can also find use in a agrobiology, as stable plant protectants, as activators of the defence mechanisms and growth regulators of the plant cell similarly as has been described with N-acetyl-chitooligosaccharides and their acyl derivatives (13). In such use, incorporation of the fucose group in the oligosaccharide will in practice protect the oligosaccharide from enzymatic degradation.

The α1–3/4fucosylated analogues of animal oligosaccharides are useful for studies of biological interactions involving their natural counterparts. The natural α1–3/4fucosylated oligosaccharides are known to be ligands or counterreceptor of lectins mediating cell adhesion and other intercellular interactions. These saccharides are also important antigenic epitopes recognized by anti-cancer or allergy-related antibodies. Some of these interactions are of special medical interest such as the leukocyte adhesion to blood vessels mediated by the binding of the selectin proteins to their α1–3/4fucosylated counterreceptor oligosaccharides linked to proteins or lipids. The free oligosaccharide analogues can be tested in in vitro or in vivo assays to find out their abilities to inhibit the binding between the lectins and their counterreceptors or alternatively the direct binding of the oligosaccharides to the lectins can be measured for example by affinity chromatography. The data obtained with the analogues in comparison to free saccharide epitopes identical to the natural counterreceptor oligosaccharides reveal part of the specificity of the interaction. It shows which modifications in the molecule are useful and which are not tolerated when better medical lead compounds for antagonists of the interaction are designed. In search of better medical derivatives of the oligosaccharides the reducing end of the oligosaccharide chain can be modified by numerous non-carbohydrate structures, aglycons. Free oligosaccharides can also be useful as mixture of known composition (so called libraries) in the tests of biological activities. Mixtures of positional fucosyl isomers are easily obtained by incubating oligosaccharide with multiple acceptor sites with less GDP-Fuc than the amount of the acceptor sites or by following the reaction level by MALDI-TOF analysis of the reaction mixture and limiting the reaction time (14).

Multi- or polyvalent conjugates of the oligosaccharides can also be more active antagonists of biological interactions when they are of natural and non-antigenic type. Antigenic polyvalent conjugates such as oligosaccharides coupled to bovine serum albumin or to keyhole limpet hemocyanin can be used to raise antibodies against the saccharide epitopes. Polyvalent conjugates conjugated to solid supports, such as agarose affinity chromatography media or plastic micro titer plates, are also useful for assaying and purification of lectins and other proteins binding the saccharides. Fucosylated N-acetyl-chitooligosaccharide epitopes —Manβ1–4GlcNAc (Fucα1–3)GlcNAcβ1-Asm of plant and insect proteins (15) are potent and cross relative human allergens and GlcNAc(Fucα1–3)GlcNAcβ1-conjugates can be useful for assaying allergy antibodies recognizing the epitope.

The selection proteins mediating vascular leukocyte adhesions are known to bind sialyl-Lewis x [sLex, NeuNAcα2–3Galβ1–4(Fucα1–3)GlcNAc], especially in sLexβ1–3Lexβ1-(16), and sialyl-Lewis a [NeuNAcα2–3Galβ1–3(Fucα1–4)GlcNAc] oligosaccharides (17) and in some reports also Lewis x [Lex, Galβ1–4 (Fucα1–3)GlcNAc] (18) or VIM-2 epitopes [NeuNAcα2–3Galβ1–4GlcNAcβ1–3Galβ1–4(Fucα1–3) GlcNAc] (19). GalNAc-analogue of Lewis x, GalNAcβ1–4 (Fucα1–3)GlcNAc has been reported to be better selectin ligand than the sialyl-Lewis x (20, 21).

The following examples are intended to illustrate the invention.

The products according to the invention have been characterized by degradation, mass spectrometry and NMR-experiments. The latter suggest that the non-reducing end monosaccharide and the fucose are stacked in a solution conformation reminiscent of that dominating in Lex and LexNAc determinants. This lends significant protection to the fucosylated oligosaccharides.

In the examples the following abbreviations have been used:

DQFCOSY, double quantum filtered correlation spectroscopy; ESI-CID, electrospray ionization-collision induced decay; Fuc & F, L-fucose; Fuc-Ts III–VIII and IX, human α1–3fucosyltransferases/α1–3/4fucosyltransferases III–VII and IX; Fuc-Thm, α1–3/α1–3/4fucosyltransferases of human milk; Gal, D-galactose; GalNAc, D-N-acetylgalactosamine; GlcNAc & GN, D-N-acetylglucosamine; HPAEC-PAD, high pH anion exchange chromatography—pulsed amperometric detection; LacNAc, Galβ1–4GlcNAc; LacdiNAc, GalNAcβ1–4GlcNAc, MALDI-TOF MS, matrix-assisted laser desorption/ionization time of flight mass spectrometry; m/z, mass to charge ratio; MOPS, 3-[N-Morpholino]propanesulphonic acid; ROESY, rotating frame nuclear Overhauser spectroscopy; ROE, rotating frame nuclear Overhauser; TOCSY, total correlated spectroscopy In the examples, N-acetyl-chitotriose, N-acetyl-chitotetraose, and N-acetyl-chitohexaose were from Seikagau (Tokyo, Japan). Cellobiose was from Thomas Kerfoot and Co.Ltd., and β-N-acetylhexosaminidase from jack beans was from Sigma (St. Louis, Mo. U.S.A.). GDP-fucose (used in human milk experiments) was a kind gift from Prof. B. Ernst (Universität Basel, Switzerland). Human fucosyltransferases V and VI, recombinant proteins expressed in *Spodeptera frugiperda*, and GDP-fucose were from Calbiochem (La Jolla, Calif., U.S.A.). GDP-[U-$^{14}$C]fucose was from Amersham International (Buckinghamshire, England). Superdex Peptide HR 10/30 HPLC-column was from Pharmacia (Uppsala, Sweden). Dowex AG 1-X8 (AcO$^-$, 200–400 mesh) and Dowex AG 50W-X8 (H+, 200–400 mesh) and Biogel P-2 were from Bio-Rad (Richmond, Calif.). D$_2$O was from Cambridge Isotope Laboratories (Woburn, Mass.). Partially purified human milk fucosyltransferases were prepared as described in (22) and assayed as described in (23), 1 mU corresponds to transfer of 1 nmol of fucose to 190 mM lactose/minute at 37° C., pH 7.5.

Fucosyltransferase reactions:

Fucosylation of N-acetyl-chitooligosaccharides with human milk fucosyltransferases (EC 2.4.1.152 and EC 2.4.1.65) was carried out essentially as described in (24), but with 2*360 μU of the enzyme (adding half of the enzyme after 2 days)/100 μl of reaction mixture and the acceptor concentrations were 5 mM and by incubating reactions at 37° C. for four days. Fucosyltransferase V (Fuc-TV, EC 2.4.1.152, recombinant, Calbiochem) reactions were carried out under similar conditions but with 12.5 mU of the enzyme/100 μl, and the reaction mixtures were incubated at room temperature for five days. Vast excesses of GDP-Fuc in comparison to expected amount of products were used. Fucosyltransferase VI (EC 2.4.1.152, recombinant, Calbiochem) reactions were carried out under the same reaction conditions as with Fuc-TV except 2 mM acceptor and 4 mM GDP-Fucose concentration and 10 mU of the enzyme/100 μl, and incubation for 3 days at 37° C. The reactions were terminated by boiling for 3 minutes, the reaction mixtures were stored frozen until analysed.

β-N-acetylhexosaminidase reactions.

Reactions catalyzed by jack bean β-N-acetylhexosaminidase (EC 3.2.1.30) under mild conditions were performed as described (25), using 0.3 mU of the enzyme/nmol releasable GlcNAc or in endochitinase reactions with Fuc$_1$GN$_{4,6}$ 6 nmol of saccharides were incubated 11 h with 38 mU of the enzyme.

Reactions performed under exhaustive reactions contained 300 mU of the β-N-acetylhexosaminidase in 4.8 μl of 2.5 M (NH$_4$)$_2$SO$_4$, 2 nmol of fucosylated N-acetyl-chitooligosaccharides, and 40.2 μl of 50 mM sodium citrate pH 4.0. The reactions were incubated at 37° C., 300 mU of fresh enzyme in 2.5 M (NH$_4$)$_2$SO$_4$ was added on days 2,3,5 and 7, and the reactions were stopped at day 8 by adding 1 vol of ice-cold ethanol and 8 volumes of ice-cold water.

Reduction of oligosaccharides.

Oligosaccharides were reduced with NaBH$_4$ essentially as described in (26). The alditols were purified by gel filtration and the completeness of the reactions was verified by MALDI-TOF mass spectrometry.

Chromatographic methods.

Samples from the enzymatic reactions were desalted by passing them in water through 1.5 ml of Dowex AG-50 (H+, 200–400 mesh) and 1.5 ml of Dowex AG-1 (AcO-, 200–400 mesh) and then purified by gel filtration HPLC in a column of Superdex Peptide HR 10/30, with ultra pure water or 50 mM $NH_4HCO_3$ as eluant, at a flow rate of 1 ml/min. Gel filtration in a Biogel P-2 columns (1×142 cm) was performed with ultrapure water, UV-absorbance was monitored at 214 nm. High-pH anion exchange chromatography with pulsed amperometric detection (HPAEC-PAD) was performed on a (4×250 nm) Dionex CarboPac PA-1 column (Dionex, CA), the samples were run isocratically with 40 or 60 mM NaOH.

Mass spectrometry.

Matrix-associated laser desorption/ionization time-of-flight mass spectrometry (MALDI-TOF MS) was performed in the positive ion delayed extraction mode with a BIFLEX™ mass spectrometer (Bruker-Franzen Analytik Bremen, Germany) using 2,5-dihydroxybenzoic acid as the matrix. The matrix peaks at the low mass region were "suppressed" by using high sample concentrations (100 pmol/$\mu$l).

Electrospray mass spectra (ESI-MS) were collected using an API365 triple quadrupole mass spectrometer (Perkin-Elmer instruments, Thornhill, Ontario, Canada). Samples were dissolved in 50% aqueous methanol containing 0.5 mM sodium hydroxide, and injected into the mass spectrometer with a nanoelectrospray ion source (Protana A/S, Odense, Denmark) at a flow rate of about 30 nl/min. MS/MS spectra were acquired by colliding the selected precursor ions to nitrogen collision gas with acceleration voltages of 35 V (doubly-charged precursors) or 55 V (singly charged precursors).

NMR spectroscopy.

Prior to NMR experiments the saccharides were lyophilized twice from $D_2O$ with then dissolved in 300 $\mu$L of $D_2O$ (99.996 atom %, Cambridge Isotope Laboratories, Woburn, Mass., U.S.A.). The NMR experiments were carried out on a Varian Unity 500 spectrometer at 23° C. using Shigemi tubes (Shigemi Co., Tokyo, Japan). In recording ID proton spectra a modification of the WEFT sequence (27) was used. For the DQFCOSY (28) and TOCSY (29) experiments (32 scans per $t_1$ value) matrices of 2k*256 and 4k*256 points were collected, and zero-filled to 2k*512 and 4k*512 points, respectively. A 90° shifted sine-bell weighting function was employed in both dimensions. In TOCSY, a spin-lock time of 100 ns (MLEV-17) was used. In order to resolve overlap within spin systems 1D selective TOCSY (30) spectra were recorded with mixing times varying from 10 ms to 140 ms and a gaussian selective pulse. In recording the ROESY spectrum (31, 32) the transmitter was placed outside the signal area at 5.750 ppm and a continuous-wave spin-lock with spin-lock time of 300 ms was employed. A matrix of 2k*256 was collected and zero-filled to 2k*512 points. A 90° shifted sine-bell weighting function was used in both dimensions. Additionally, the $t_1$ time domain data was doubled using forward-backward linear prediction.

For the DEPT(135) (33) spectrum 92,000 points were recorded with a spectral width of 18,000 Hz. For the HSQC (34) and 2D HSQC-TOCSY (35) (48 and 56 scans per $t_1$ value, respectively), matrices of 2k*128 and 2k*256 points were recorded and zero-filled to 2k*256 and 2k*512 points, respectively and a shifted sine-bell function was used. In the 2D HSQC-TOCSY a mixing time of 120 ms was employed. The $^1$H and $^{13}$C chemical shifts were referenced to internal acetone, 2.225 and 31.55 ppm, respectively.

EXAMPLE 1

Human Fuc-TV-catalyzed reaction of N-acetyl-chitotriose and GDP-Fucose

The oligosaccharide mixture, generated by incubation of N-acetyl-chitotriose (1000 nmol, 5 mM) with GDP-Fuc (1000 nmol, 5 mM) and 25 mU Fuc-TV at room temperature for 5 days was desalted and isolated by gel filtration HPLC. MALDI-TOF-MS revealed that the mixture contained 32 mol % fucosylated N-acetyl-chittotriose and 68% N-acetyl-chitotriose. This mixture was subjected to the "mild treatment" with jack bean $\beta$-N-acetylhexosaminidase, which cleaved most of the surplus N-acetyl-chitotriose substrate but only a small amount of the fucosylated N-acetyl-chitotriose product. A representative sample of all oligosaccharides was isolated from a 5% aliquot of the digest by using gel filtration HPLC. MALDI-TOF MS analysis of showed that it consisted of fucosylated N-acetyl-chitotriose 67 mol %, N-acetyl-chitotriose 7%, $Fuc_1GlcNAc_2$ 12%, N-acetyl-chitobiose 13%.

The monofucosylated N-acetyl-chitotriose was purified from the rest of the $\beta$-N-acetylhexosaminidase digest by gel filtration HPLC. MALDI-TOF-MS analysis of the purified $Fuc_1GlcNAc_3$, Glycan 3, revealed the presence of only a 5% N-acetyl-chitotriose contamination. The total yield of the purified Glycan 3 was 191 nmol (19%).

Mass spectrometric characterization of Fuc-TV generated Glycan 3

Figure 3:
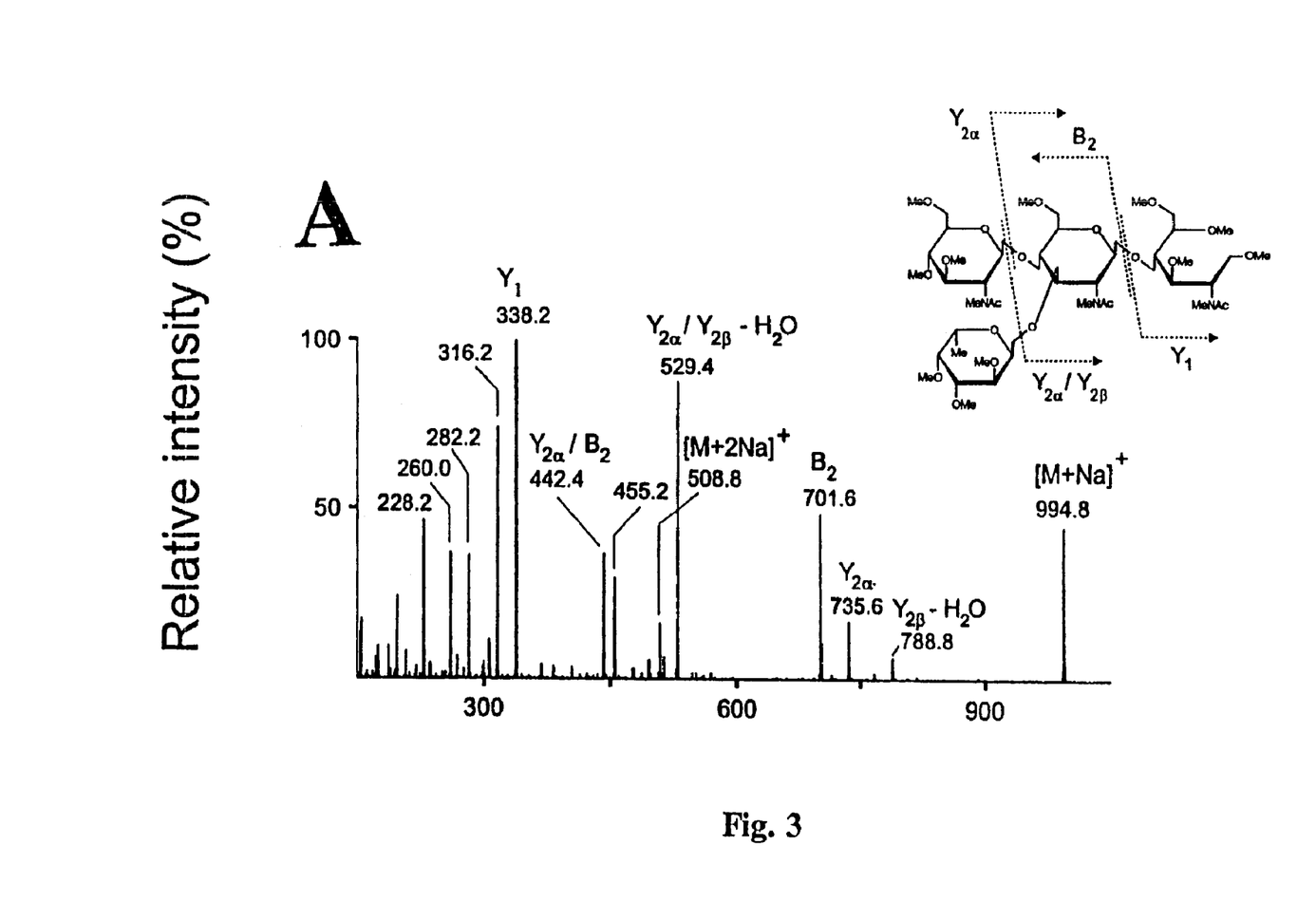
FIG. 3. shows MS/MS spectra of reduced and permethylated fucosylated N-acetyl-chitotriose 3 (A), and N-acetyl-chitotetraose 4 (B). The fragment ion nomenclature of Domon and Costello is used to denote the generated fragments.

An aliquot of the monofucosylated N-acetyl-chitotriose was reduced and permethylated and subjected to ESI-MS. The doubly-charged $[M+2Na]^{2+}$ ion (m/z 508.8) was first selected for MS/MS (FIG. 3A). The fragments obtained could all be assigned to a tetrasaccharide carrying the fucose unit in the middle GlcNAc units, i.e. GlcNAc$\beta$1-(Fuc$\alpha$1-)GlcNAc$\beta$1-GlcNAcol. A loss of terminal, nonsubstituted GlcNAc unit is evident from the $B_1$ ions at m/z 282.2 (sodiated) and m/z 260.0 (protonated). Loss of methanol from the m/z 260.0 ion accounts for the m/z 228.2 and m/z 196.2 ions. The $Y_1$ ions at m/z 316.2 and m/z 338.2 (carrying one and two sodiums, respectively) indicate that the GlcNAc alditol carried only one monosaccharide substitutent. Furthermore, the $Y_{2\alpha}/B_2$ ion at m/z 442.4 can only arise by loss of terminal unsubstituted GlcNAc and the reduced GlcNAc residue. No fragments were observed even in closer inspection, which would represent fucosylated reduced end (i.e. Fuc$\alpha$1-GlcNAcol, m/z 490.4) or fucosylated nonreducing end GlcNAc (terminal Fuc$\alpha$1-GlcNAc, m/z 456.2). The origin of the fairly intense fragment at m/z 455.2 is somewhat complex. Its nature was revealed by producing the $B_2$, $Y_{2\alpha}$ and $Y_{2\beta}$-H2O fragments with a high orifice voltage, and by collecting MS/MS/MS data with these skimmer fragments (not shown). Only the Y ions generated the m/z 455 ion, so it must contain the reducing end. We suggest that this is an $^{0,4}X_1$ ion, arising by a cross-ring cleavage of the penultimate GlcNAc ring.

NMR-spectroscopy of Fuc-TV generated Glycan 3

The data from 1D 1H-NMR-spectrum of Fuc-TV-generated Glycan 3 is reported in Table 2. Table 1 indicates the number of the residues used in Table 2. The H1, H5 and H6 signals of fucose in Glycan 3 resemble their counterparts in GlcNAc$\beta$1–4(Fuc$\alpha$1–3)GlcNAc glycans (36) and in Glycan 4 analyzed by 2D NMR (Table 2), but are distinct from those in —GlcNAc$\beta$1–4(Fuc$\alpha$1–6)GlcNAc saccharides (37). Taken together, the NMR-data confirm that the fucosylated N-acetyl-chitotriose, Glycan 3, generated by Fuc-TV is GlcNAc$\beta$1–4(Fuc$\alpha$1–3)GlcNAc$\beta$1–4GlcNAc.

The reaction of N-acetyl-chitotriose and GDP-Fucose catalyzed by human milk Fuc-Ts Incubation of N-acetyl-chitotriose (1000 nmol, 5 mm) with GDP-fucose (600 nmol, 3 mM) and 1.4 mU of the enzyme for four days at 37° C. gave an oligosaccharide mixture. After ion exchange desalting, mild β-N-acetylhexosaminidase treatment, and repeated gel filtration HPLC runs, a sample of 221 nmol of purified fucosylated N-acetyl-chitotriose was obtained. MALDI-TOF MS revealed that the product contained 92% of fucosylated N-acetyl-chitotriose and 7% of N-acetyl-chitotriose. The 1D 1H-NMR-spectrum of the product was almost identical with that of Fuc-TV-generated Glycan 3. The ESI-MS-data of the Glycan 3 in reduced form, too, were identical to those obtained with reduced derivative of the Fuc-TV-generated Glycan 3 (not shown).

EXAMPLE 2

The Fuc-TV-catalyzed reaction of N-Acetyl-Chitotetraose and GDP-Fucose

Figure 2:
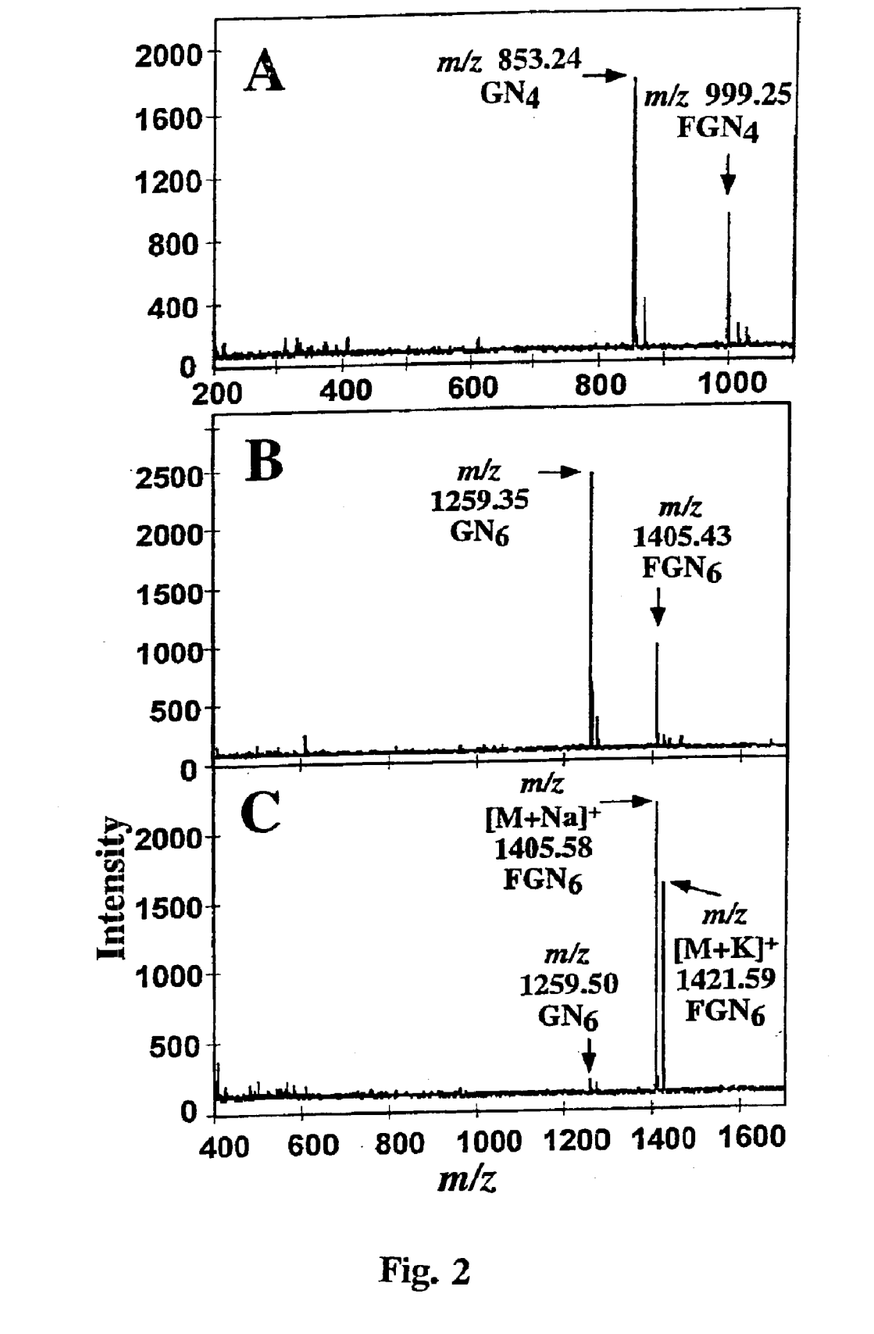
FIG. 2 shows MALDI-TOF mass spectra of the key reaction mixtures and purified product saccharides. F is L-Fucose, GN is N-acetyl-D-glucoseamine. (A) shows a mixture of $FGN_4$ produced by human Fuc-TV, (B) shows a mixture of $FGN_6$ and $GN_6$ produced by Fuc-TV. (C) shows $FGN_6$ purified by HPAE-chromatography. (D) shows exo-β-N-acetylhexosaminidase and novel endo-chitinase (the jack bean enzyme, mild conditions) reaction to the mixture of $FGN_6$ and $GN_6$ produced by Fuc-TV. The major product is surprisingly $FGN_5$. (E) shows mild cleavage of the purified $FGN_6$ to mostly $FGN_5$ by the jack bean preparation. (F) shows mild treatment of the purified $FGN_4$ by the jack bean preparation, 91% of the substrate remains intact.

Incubation of N-acetyl-chitotetraose (1000 nmol, 5 mM) with GDP-Fuc (1000 nmol, 5 mM) and 25 mU human Fuc-TV at room temperature for 5 days, and isolation of the resulting oligosaccharide mixture by using gel filtration HPLC gave a product consisting of 32 mol % fucosylated N-acetyl-chitotetraose and 68% of unreacted N-acetyl-chitotetraose (FIG. 2A). The mild treatment of the mixture with jack bean β-N-aceylhexosaminidase followed by chromatographic removal of the liberated from GlcNAc gave an oligosaccharide mixture consisting of $Fuc_1GlcNAc_4$ 50%, $GlcNAc_4$ 6%, $Fuc_1GlcNAc_3$ 8%, $GlcNAc_3$ 14%, $GlcNAc_2$ 22 mol %. The composition of this mixture implies that also the fucosylated N-acetyl-chitotetraose was cleaved much slower than N-acetyl-chitotetraose by the β-N-acetylhexosaminidase, confirming the analogous data on degradation of Glycan 3. The oligosaccharide mixture was then fractioned by gel filtration HPLC, yielding a purified product (225 nmol) that consisted of 93 mol % of fucosylated N-acetyl-chitotetraose and 7% N-acetyl-chitotetraose.

Figure 1:
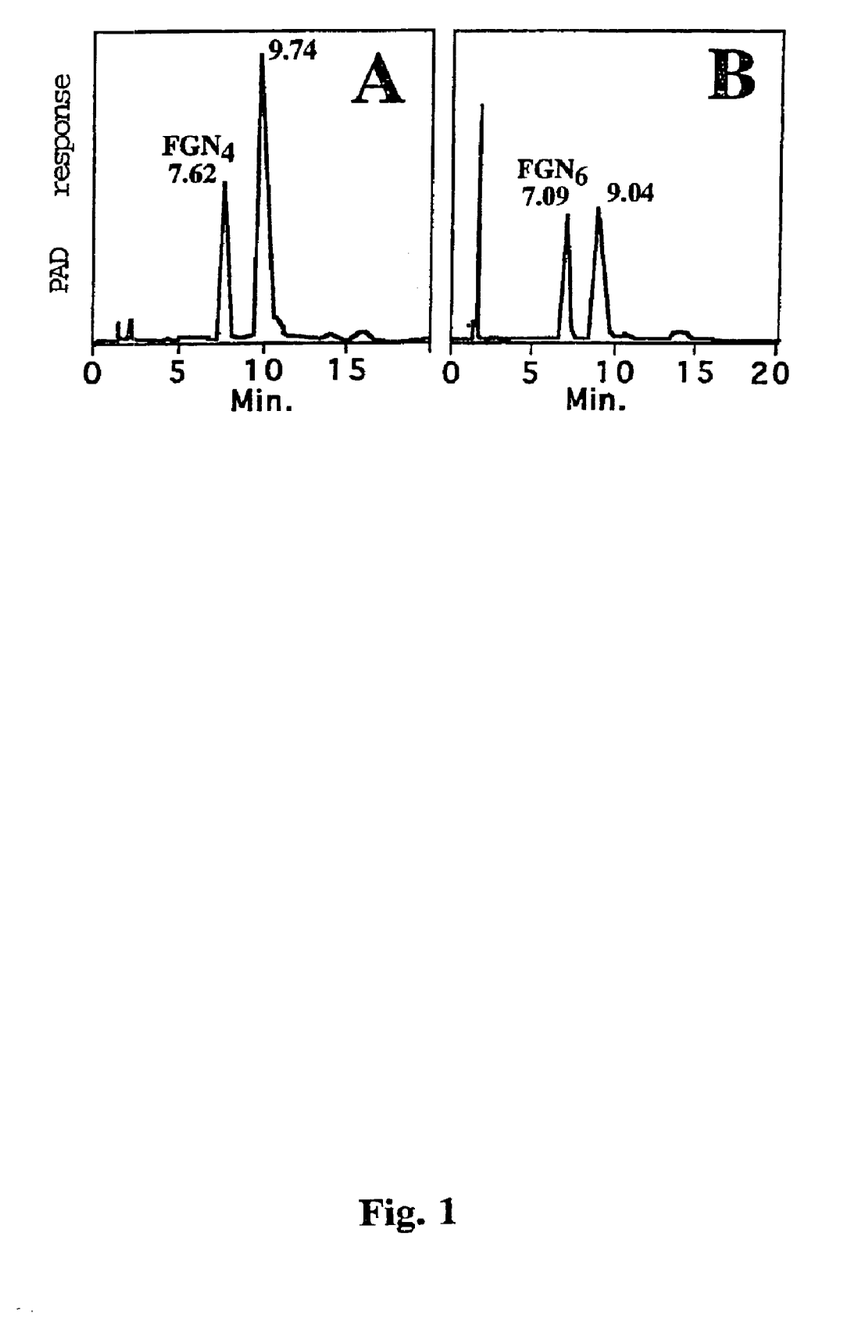

Another fucosylation mixture consisting of 11% of the fucosylated N-acetyl-chitotetraose and 89% of N-acetyl-chitotetraose was separated in an isocratic HPAE run in a (4×250 mm) Dionex CarboPac PA-1 column (Dionex, Sunnyvale, Calif.) column by using with 40 mM NaOH as the eluent (FIG. 1A). The peak eluting at 7.62 min contained the fucosylated N-acetyl-chitotetraose. The 1D 1H-NMR spectrum of the purified product, Glycan 4 synthesized by Fuc-TV was almost identical with that of Glycan 4 synthesized by the Fuc-Ts of human milk (see below).

A sample of the purified Glycan 4 was degraded by the exhaustive treatment with jack bean β-N-acetylhexosaminidase, yielding an oligosaccharide that behaved in gel filtration as a compound about 1.5 glucose unit smaller then N-acetyl-chitotetraose, suggesting that it had lost a GlcNAc unit. This view was confirmed by applying MALDI-TOF-MS analysis, which revealed 89 mol % $Fuc_1GlcNAc_3$ and 11 mol % $Fuc_1GlcNAc_2$. The minor product species had probably lost both the non-reducing end GlcNAc and the reducing end GlcNAc during the exhaustive cleavage (see below, at the mild jack bean β-N-acetylhexosaminidase treatment of the fucosylated N-acetyl-chitohexaose).

Put together, the analytical data of Fuc-TV generated Glycan 4 are consistent with the structure of GlcNAcβ1–4 (Fucα1–3(GlcNAcβ1–4GlcNAcβ1–4GlcNAc.

Glycan 4-synthesis catalyzed by human milk Fuc-Ts

N-Acetyl-chitotetraose (6.0 μmol, 5 mM), and GDP-Fuc (3.0 μmol, 2.5 mM) were incubated with 8.7 mU of the enzyme for four days at 37° C. After desalting and gel filtration HPLC-run, the fucosylated product was separated from the non-fucosylated N-acetyl-chitotetraose by HPAEC using isocratic run with 40 mM NaOH (not shown). The purified product was desalted by ion exchange and was further purified by gel filtration HPLC yielding 744 nmol monofucosylated N-acetyl-chitotetraose. MALDI-TOF mass spectrometry of the product revealed that it was uncontaminated by N-acetyl-chitotetraose acceptor (not shown).

A sample of the purified Glycan 4 generated by human milk Fuc-Ts was treated exhaustively with jack bean β-N-acetylhexosaminidase. MALDI-TOF-MS analysis of the HPLC-purified oligosaccharides of the digest revealed 91 mol % $Fuc_1GlcNAc_3$ and 9% $Fuc_1GlcNAc_2$.

Mass spectrometric characterization of Glycan 4 generated by human milk Fuc-Ts

An aliquot of the monofucosylated N-acetyl-chitotetraose was reduced and permethylated and subjected to ESI-MS. The doubly-charged $[M+2Na]^{2+}$ ion (m/z 631.6) was selected for MS/MS (FIG. 3B). The low-mass region of the MS/MS spectrum resembles that of the monofucosylated N-acetyl-chitotriose, showing the same $B_1$ fragment s for the unsubstituted terminal GlcNAc unit (m/z 282.2, m/z 260.2), and $Y_1$ ions for the reducing end GlcNAc alditol (m/z 316.2, m/z 338.2).

In addition, the $Y_{2\alpha}/B_2$ ion (m/z 442.4), the $B_3$ ion (m/z 946.8), and the $Y_{3\alpha}$ ion (m/z 980.6) verify that the fucose unit is linked to either of the midchain GlcNAc units. The $Y_2$ ion at m/z 561.4 indicates that this disaccharide fragment only carried one monosaccharide substituent, and thus the fucose must reside at the penultimate GlcNAc residue. This is directly confirmed by the $B_2$ ion at m/z 701.6, carrying the non-reducing terminus structure GlcNAcβ1-(Fucα1-)GlcNAc. Even closer investigation of the minute fragments in the MS/MS data did not reveal any specific fragments for other pentasaccharide isomers, and we therefore conclude that N-acetyl-chitotetraose is fucosylated solely to the penultimate GlcNAc residue next to the non-reducing end.

NMR-spectroscopic analysis of Glycan 4 produced by human milk Fuc-Ts

The 1D 1H-NMR spectrum of the purified product, Glycan 4 (Table 3) revealed fucose H1, H5 and H6 signals characteristic to α3-linked fucose rather than α6-linked fucose in unconjugated N-glycans (36, 37). The H4 signal of the distal GlcNAc6 was similar to its analogs in Glycan 3, confirming that the fucose is linked to the penultimate GlcNAc unit close to the non-reducing end. The proton signals of the fucose and the non-reducing end GlcNAc6 were assigned from DQFCOSY and TOCSY spectra of Glycan 4. The 2NMR-data strengthen the notion that the non-reducing end elements of Glycan 4 resemble those of Glycan 3.

Taken together, the NMR-data confirm the MS-results and the degradation data, establishing that Glycan 4 generated by human milk Fuc-Ts represented also GlcNAcβ1–4 (Fucα1–3)GlcNAcβ1–4GlcNAcβ1–4GlcNAc.

EXAMPLE 3

Human FucTV-Catalyzed Reaction of N-Acetyl-Chitohexaose and GDP-Fucose

N-Acetyl-chitohexaose (1.0 μmol, 5 mM) was fucosylated with GDP-Fucose (1.0 μmol, 5 mM) and 25 mU Fuc-TV at room temperature for 5 days. MALDI-TOF MS of the purified representative mixture of the product oligosaccharides showed that 31% of N-acetyl-chitohexaose was fucosylated (FIG. 2B). The product saccharides were further purified in in HPAE-chromatography run isocratically with 40 mM NaOH (FIG. 1B). The peak eluting at 7.09 min was pooled, was desalted and was further purified by gel filtration HPLC. The product heptasaccharide (195 nmol) showed in MALDI-TOF analysis 96% of monofucosylated N-acetyl-chitohexaose, Glycan 6, and 4% of N-acetyl-chitohexaose, FIG. 2C. The 1D 1H NMR spectrum (Table 2) shows the H1 signals in the GlcNAc5, the GlcNAc6 and the fucose units in Glycan 6, which are nearly identical with their counterparts in Glycan 4. This suggests that the Glycan 6 is GlcNAcβ1–4(Fucα1–3)GlcNAcβ1–4GlcNAcβ1–4GlcNAcβ1–4GlcNAcβ1–4GlcNAc. This notion is further supported by the identical H4-signals of the distal GlcNAc6 units and the fucose H5 resonances in the two glycans. The similarity of this latter pair of signals in the two glycans is particularly significant, because they are known to interact in Glycan 4 (see above), and are likely to be very sensitive to structural differences. Likewise, the similarity of fucose H5 signals in Glycan 6, and Glycan 4 speaks for the identity of the nonreducing area in these three saccharides.

Treatment of Glycan 6 with jack bean β-N-acetylhexosaminidase

A Fuc-TV-generated mixture of Glycan 6 and N-acetyl-chitohexaose (27:73 mol/mol (FIG. 2B)) was subjected to the mild jack bean β-N-acetylhexosaminidase treatment as described earlier. The resulting oligosaccharides were isolated as a representative mixture by using gel filtration HPLC. MALDI-TOF MS revealed that mixture consisted of $Fuc_1GlcNAc_6$ (3.5 mol %), $GlcNAc_6$ (1.7%), $Fuc_1GlcNAc_5$ (40%), $Fuc_1GlcNAc_4$ (3.5%); small N-acetyl-chitooligosaccharides ranging from N-acetyl-chitobiose to N-acetyl-chitopentaose were also observed (FIG. 2D). The principal product of the digest, the monofucosylated N-acetyl-chitopentaose, Glycan 5, was purified in a gel filtration HPLC-run. MALDI-TOF MS suggested that Glycan 5 was obtained hereby in a purity of 83%; it was contaminated by several penta- and hexasaccharides. The chemical shifts are presented in Table 2. The NMR data show nearly identical H1 signals in the GlcNAc5, the GlcNAc6 and the fucose units in Glycan 5 and Glycan 4, suggesting, that the structure of the former is GlcNAcβ1–4(Fucα1–3)GlcNAcβ1–4GlcNAcβ1–4GlcNAc.

This notion is further supported by the identical H4-signals of the distal GlcNAc6 units and the fucose H6 resonances in the two glycans. Hence, the mild jack bean β-N-acetylhexosaminidase treatment has surprisingly released a GlcNAc unit from the reducing end of Glycan 6, but has not attacked the reducing end of the product, Glycan 5, as efficiently.

Treatments of purified Glycan 6 and Glycan 4 by the endo-chitinase activity of jack bean β-N-acetylhexosaminidase When the purified Fuc-TV-generated Glycan 6 was subjected to the mild treatment with jack bean β-N-acetylhexosaminidase, the resulting digest showed in MALDI-TOF MS only 5 mol % of intact substrate; 85% of the material was converted into $Fuc_1GlcNAc_5$ and 11% into $Fuc_1GlcNAc_4$ (FIG. 2E). The data confirms that the endo-chitinase cleaves fast Glycan 6, releasing mainly one GlcNAc unit from the reducing end and the enzyme may be able to cleave off also a N-acetyl-chitobiose unit from the reducing end of Glycan 6, generating Glycan 4. Alternatively, Glycan 4 may have been formed by the release of a GlcNAc unit from the reducing end of $Fuc_1GlcNAc_5$.

When the purified Fuc-TV-generated Glycan 4 was subjected to the mild treatment with jack bean β-N-acetylhexosaminidase, the resulting digest showed in MALDI-TOF MS that most (91 mol %) of the substrate had survived and only 6% of $Fuc_1GlcNAc_3$ had been formed; 3% of the material was found as fucose-free N-acetyl-chitotetraose (FIG. 2F). Hence, the endo-chitinase activity appeared to cleave off slowly one GlcNAc unit from the reducing end of Glycan 4.

EXAMPLE 4

Fucosylation of cellobiose

Cellobiose (4000 nmol, 20 mM, from Thomas Kerfoot and Co. ltd) was incubated with GDP-[$^{14}$C]Fuc (1000 nmol, 5 mM, 100 000 cpm) and recombinant fucosyltransferase V (25 mU, 50 ml of the commercial enzyme preparation from Calbiochem) in 50 mM MOPS-NaOH pH 7.5 containing 8 mM $MnCl_2$, 1000 mM NaCl, 1 mg/ml BSA and 0.02% $NaN_3$ in total volume of 200 ml at room temperature for 4 days and 16 hours. The reaction products were desalted by running through 1.5 ml beds of Dowex AG 1-X8 and Dowex AG 50W-X8. Part of the products were run in paper chromatography which showed a trisaccharide like product migrating close to maltriose (Rmaltotriose=0.97 marker, glycerol in the sample may affect the migration) and a broad peak (broadened by glycerol in the sample) probably corresponding to free [$^{14}$C]Fuc. Solvent A was used as described in (38), using the upper phase of n-butanol-acetic acid:water (4:1:5, v/v, solvent A) and scintillation counted from small strips of paper. Major part (75%) of the products were run in gel filtration chromatography in Biogel P-2 (Biorad) column. A peak of radioactive products (256 nmol by radioactivity, calculated total yield 340 nmol) eluting at position expected for monofucosylated cellobiose was obtained and another radioactive peak containing [$^{14}$C]Fuc-like material. Fractions in the first half of the product peak were analyzed to contain saccharide with size corresponding to fucosylated cellobiose in MALDI-TOF mass spectrometry, monoisotopic m/z [M+Na]+ close to 511.2 and m/z [M+K]+ close to 527.2, the fractions contained very minor amounts or no other possible saccharides like cellobiose or cellotriose. The pooled saccharide (150 nmol by radioactivity) were analyzed by NMR-spectroscopy. NMR-spectroscopy revealed signals of Fuc H1α at 5.425 ppm, Fuc H1β at 5.369 ppm and signals of the reducing Glc H1a at 5.189 ppm and Glc H1β at 4.655 ppm similarly as described for —Galβ1–4(Fucα1–3)Glc (39).

A product (<0.5 pmol) migrating similarly in paper chromatography (Rmaltotriose=1.04) can be obtained by incubating lysate (40 mg of protein) of CHO-cells expressing full length Fuc-TV with GDP-[$^{14}$C]Fuc (1 nmol, 100 000 cpm) and 100 nmol of cellobiose for 1 hour as described in (40).

EXAMPLE 5

Reactions with laminaribiose and laminaritetraose
Glcβ1–3Glc+GDP-Fuc→Glcβ1–3(Fucα1–4)Glc
Glcβ1–3Glcβ1–3Glcβ1–3Glc+GDP-Fuc→
Glcβ1–3(Fucα1–4)Glcβ1–3Glcβ1–3Glc
+Glcβ1–3Glcβ1–3(Fucα1–4)Glcβ1–3Glc
+Glcβ1–3Glcβ1–3Glcβ1–3(Fucα1–4)Glc Laminaribiose (1000 nmol, 5 mM, Seikagaku) and laminaritetraose (1000 nmol, 5 mM, Seikagaku) were reacted with GDP-[$^{14}$C]Fuc (1000 nmol, 5 mM, 100 000 cpm) and recombinant fucosyltransferase V (25 mU, 50 ml of the commercial enzyme preparation from Calbiochem) as above. The products of both reactions were desalted as above. The products from laminaribiose were purified by P-2 gel filtration chromatography and radioactive trisaccharide-like product was obtained.

The desalted products from laminaritetraose were also purified by P-2 gelfiltration chromatography and a radioactive (174 nmol by radioactivity) peak eluting a pentasaccharide product as expected, was obtained, 131 nmol of product with monoisotopic m/z [M+Na]$^+$ close (difference less than 0.1%) to 835.3 and m/z [M+K]$^+$ close to 851.3 were pooled from front and middle fractions of the peak, the fractions contained less than 4% of the acceptor, no other saccharide products were observed in analysis by MALDI-TOF mass spectrometry. The purified product saccharides were analyzed by NMR spectroscopy.

EXAMPLE 6
Desulfation, reduction, and fucosylation of chondroitin sulfate

Chondroitin sulfate (shark cartilage, Sigma) was cleaved by hyaluronidase (bovine testes, Sigma; chondroitin sulfates can be also cleaved with chondroitinases giving oligosaccharides with delta-uronic acid at non reducing end) to sulfated oligosaccharides such as[GlcAβ1–3(sulf-6)GalNAcβ1–4]nGlcAβ1–3(sulf-6)GalNAc. Fractions containing tetrasaccharide-like materials were purified and desulfated as essentially as described in (41). Tetrasaccharide and hexasaccharide fractions were purified by gel filtration and anion exhange chromatographies. Similar oligosaccharides were also produced by first desulfating and then cleaving by hyaluronidase and purifying the products. The GlcA-residues of the tetrasaccharide were reduced to Glc by EDAC (1-ethyl-3-(3-dimethylaminopropyl)carbodiimide) and NaBH$_4$. The reduced tetrasaccharide Glcβ1–3GalNAcβ1–4Glcβ1–3GalNAcol was purified and fucosylated using GDP-Fuc and human milk fucosyltransferase(s). The MALDI-TOF mass spectrometry revealed peaks at m/z 919.8 and m/z 935.8 corresponding to the product Glcβ1–3GalNAcβ1–4(Fucα1–3)Glcβ1–3GalNAcol (calc. m/z [M+Na]$^+$ is 919.7 and m/z [M+K]$^+$ is 935.7).

EXAMPLE 7

GlcNAcylβ1–4GlcNAcβ1–4GlcNAcβ1–4GlcNAc, wherein Acyl is trans-9-octadecenoyl, synthesis of the acceptor being described in (13), can be incubated with Fuc-TVI and MnCl$_2$ under conditions described above for Fuc-TVI, but acceptor concentrations between 0.1–0.5 mM are preferred. The product GlcNAcylβ1–4(Fucα1–3) GlcNAcβ1–4GlcNAcβ1–4GlcNAc is purified chromatographically and analysed by NMR-spectroscopy and mass spectrometry.

EXAMPLE 8

N-Acetyl-chitotetraose can be incubated with human Fuc-TVI and MnCl$_2$ under conditions described above for Fuc-TVI. The product GlcNAcβ1–4(Fucα1–3)(GlcNAcβ1–4GlcNAcβ1–4GlcNAc can be obtained with almost quantitative yield and purified by HPAE-chromatography. The NMR-data and mass spectroscopy data of the product are practically identical with the fucosylated N-acetyl-chitotetraose obtained by Fuc-TV.

TABLE 1

Structures of the fucosylated N-acetyl-chito-oligosaccharides in present study. GN is GlcNAc and Fuc is L-fucose, line - indicates β1-4-linkage and line / is α1-3-linkage, residue numbering is italics.

|   |                    |   |                       |
|---|--------------------|---|-----------------------|
|   | *6 5 4*            |   | *6 5 4 3*             |
| 3 | GN-GN-GN           | 4 | GN-GN-GN-GN           |
|   | Fuc/               |   | Fuc/                  |
|   | *6 5 4 3 2*        |   | *6 5 4 3 2 1*         |
| 5 | GN-GN-GN-GN-GN     | 6 | GN-GN-GN-GN-GN-GN     |
|   | Fuc/               |   | Fuc/                  |
|   | *6 5 4 3*          |   |                       |
| 7 | GN-GN-GN-GN        |   |                       |

TABLE 2

$^1$H Chemical shifts (ppm) of structural reporter groups for Glycans 3–7 at 23° C.

| Proton | Residue | Glycans 3 | 4 | 5 | 6 | 7 |
|--------|---------|-----------|---|---|---|---|
| H1 | 1 | — | — | — | 5.181(α)/4.688(β) | — |
|    | 2 | — | — | 5.182(α)/4.688(β) | 4.578/4.565* | — |
|    | 3 | — | 5.184(α)/4.689(β) | 4.579/4.567* | 4.565 | 5.185(α)/4.689(β) |
|    | 4 | 5.185(α)/4.688(β) | 4.579/4.570* | 4.567 | 4.565 | 4.58 |
|    | 5 | 4.580/4.571* | 4.570 | 4.567 | 4.565 | 4.58 |
|    | 6 | 4.522 | 4.519 | 4.517 | 4.516 | 4.58 |
|    | fucose | 5.124 | 5.119 | 5.117 | 5.116 | — |
| H4 | 6 | 3.238 | 3.237 | 3.236 | 3.235 | n.d. |
| H5 | fucose | 4.764 | 4.762 | 4.762 | 4.758 | — |
| CH3 | fucose | 1.268 | 1.267 | 1.265 | 1.264 | — | n.d. = not determined
*The two chemical shift values given arise from signals representing the α- and β-pyranosic forms of the oligosaccharides respectively.

TABLE 3

NMR-data of the Glycan 4.

| Proton | GlcNAc6 | Fucose |
|--------|---------|--------|
| H1 | 4.519 | 5.119 |
| H2 | 3.735 | 3.707 |
| H3 | 3.535 | 3.938 |
| H4 | 3.237 | 3.803 |
| H5 | 3.428 | 4.762 |
| H6 | 3.607 | — |

TABLE 3-continued

NMR-data of the Glycan 4.

| Proton | GlcNAc6 | Fucose |
|---|---|---|
| H6' | 3.963 | — |
| CH3 | — | 1.267 |

REFERENCES

1. Johnston, D. S. Wright, W. W., Shaper, J. H., Hooke, C. H., Van den Eijnden, D. H., and Joziasse, D. H. (1998) *J. Biol. Chem.* 273(4), 188–1895
2. Gooi, H. C., Feizi, T., Kapadia, A., Knowles, B. B., Solter, D., and Evans, M. J. (1981) *Nature* 292, 156–158
3. Dodd, J., and Jessel, T. M. (1986) *J. Exp. Med.* 124, 225–238
4. Oudega, M., Marani, E., and Thomeer, R. T. W. M. (1992) *Histochem. J.* 24, 869–877
5. Butcher, E. C., and Picker, L. J. (1996) *Science* 272, 60–66
6. McEver, R. P. (1997) *Glycoconjugate J.* 14, 585–591
7. Natsuka, S. Gersten, K. M., Zenita, K., Kannagi, R., and Lowe, J. B. (1994) *J. Biol. Chem.* 269, 16789–16794
8. Edbrooke, M. R., Britten, C. J., Kelly, V. A. M., Martin, S. L., Smithers, N., Winder, A. J., Witham, S. J., and Bird, M. I. (1997) *Biochem. Soc. Transact.* 25, 880–887
9. Kaneko, M., Kudo, T., Iwasaki, H., Ikehara, Y., Nishihara, S., Nakagawa, S., Sasaki, K., Shiina, T., Inoko, H., Saitou, N., and Narimatsu, H. (1999) *FEBS Lett.* 452, 237–242
10. Bergwerff, A. A., van Kuik, J. A., Schiphorse, W. E. C. M., Koeleman, C. A. M., van den Eijnden, D. H., Kamerling, J. P., and Vliegenthart, J. F. G. (1993) *FEBS Lett.* 334, 133–138
11. Bakker, H., Scoebnakers, P. S., Koeleman, C. A. M., Joziasse, D. H., van Die, I and van den Ejnden, D. H. (1997) *Glycogiology* 7, 539–548
12. Haslam, S. M., Coles, G. C., Munn, E. A., Smith, T. S., Smith, H. F., Morris, H. R., and Dell, A., (1996) *J. Biol. Chem.*, 271, 30561–30570.
13. Rohrig, H., Schmidt, J., Walden, R., Czaja, I., Miklasevics, E., Wieneke, U., Schell, J., and John M. (1995) *Science* 269, 841–843
14. Niemelä, R., Natunen, J., Penttilä, L., Salminen, H., Helin, J., Maaheimo, H., Costello, C. E., and Renkonen, O. (1999) *Glycobiology* 9, 517–526
15. Wilson, I. B. H., Harthill; J. E., Mullin, N. P., Ashford, D. A., and Altman, F. (1998) *Glycobiology* 8, 651–661
16. Wilkins, P. P., McEver, R. P., and Cummings, R. D. (1996) *J. Biol. Chem.* 271, 1873–18742
17. Varki, A. (1994) *Proc. Natl. Acad. Sci. USA* 91, 7390–7397
18. Larsen, E., Palabrica, T., Sajer, S., Gilbert, G. E., Wagner, D. D., Furie, B. C., and Furie, B. (1990) *Cell* 63, 467–474
19. Stroud, M. R., Handa, K., Salyan, M. E. K., Ito, K., Levery, S. B., Hakomori, S., Reinhold, B. B., and Reinhold, V. N. (1996) *Biochemistry* 35, 770–778
20. Jain, R. K., Piskorz, C. F., Huang, B.-G., Locke, R. D., Han, H.-L., Koenig, A., Varki, A., and Matta, K. L. (1998) *Glycogiology* 8(7), 707–717
21. Grinnell, B. W., Hermann, R. B., and Yan, S. B. (1994) *Glycobiology* 4(2), 221–225
22. Natunen, J., Niemelä, R., Penttilä, L., Seppo, A., Ruohtula, T., and Renkonen, O. (1994) *Glycobiology* 4, 577–583
23. Eppenberger-Castori, S., Lötscher, H., and Finne, J. (1989) *Glycoconjugate J.* 6, 101–114
24. Palcic, M. M., Vernot, A. P., Ratcliffe, R. M., and Hindsgaul, O. (1989) *Carbohydr. Res.* 190, 1–11
25. Renkonen, O. Helin, J., Penttilä, L., Maaheimo, H., Niemelä, R., Leppänen, A., Seppo, A., and Hård, K. (1991) *Glycoconjugate J.* 8, 361–367
26. Rasilo, M.-L., and Renkonen, O. (1982) *Hoppe Syler's Z. Physiol. Chem.* 363, 89–93
27. Hård, K., van Zadelhoff, G., Moonen, P., Kamerling, J. P., and Vliegenthart, J. F. G. (1992) *Eur. J. Biochem.* 209, 895–915
28. Marion, D., and Wüthrich, K. (1985) *Biochem. Biophys. Res. Commun.* 117, 967–974
29. Bax, A., and Davis, D. G. (1985) *J. Magn. Reson.* 65, 355–360
30. Xu, G. and Evans, J. S., (1966) *J. Magn. Reson.*, Ser. B 111, 183–185
31. Bothner-By, A. A., Stephens, R. L., Lee, J., Warren, C. D., and Jeanloz, R. W. (1984) *J. Am. Chem. Soc.* 106, 811–813
32. Bax, A., and Davis, D. G. (1985) *J. Magn. Reson.* 63, 207–213
33. Doddrell, D. M., Pegg, D. T., and Bendall, M. R. (1982) *J. Magn. Reson.* 48, 323–327
34. Kay, L. E., Keifer, P., and Saarinen, T. (1992) *J. Am. Chem. Soc.* 114, 10663–10665
35. Wijmenga, S. S. (1989) *J. Magn. Res.* 84, 634–642
36. Lhernould, S., Karamanos, Y., Bourgerie, S., Strecker, G., Julien, R., and Morvan, H. (1992) *Glycoconjugate J.* 9, 191–197
37. Lawrence, C. W., Little, P. A., Little, B. W., Glushka, J., van Halbeek, H., and Alhadeff, J. A. (1993) *Glycobiology* 3(3), 249–259
38. Renkonen, O., Penttilä, L., Makkonen, A., Niemelä, R., Leppänen, A., Helin, J. and Vainio, A. (1989) *Glycoconjugate J.*, 6, 129–140.
39. de Vries, T., Srnka, C. A., Palcic, M. M., Swiedler, S. J., van den Ejnden, D. H. and Macher, B. A., (1995) *J. Biol. Chem.* 270, 8712–8722
40. Niemelä, R., Natunen, J., Majuri, M. L., Maaheimo, H., Helin, J., Lowe, J. B., Renkonen, O. and Renkonen, R. (1998) *J. Biol. Chem.*, 273, 4021–4026.
41. Nagasawa, K., Inoue, Y. and Kamata, T. (1997) *Carbohydrate Res.*, 58, 47–55.

What is claimed is:

1. An oligosaccharide having the formula wherein A is H or a glycosidically β1–3 linked D-glucopyranosyl residue (Glcβ1–3), $R_1$ is OH, $R_2$ is H and $R_3$ is OH, acylamido or —NH-acyl or $R_1$ is H, $R_2$ is OH and $R_3$ is acetamido or —NHCOCH$_3$; B is H, an α-L-fucosyl or an α-L-fucosyl analogue, and $R_4$ is OH, acetamido or —NHCOCH$_3$, the curved line between the saccharide units indicating that the monosaccharide 1 is β1–4 linked to monosaccharide 2 when B is linked to the position 3 of the monosaccharide 2, and the monosaccharide 1is β1–3 linked to monosaccharide 2 when B is linked to the position 4 of the monosaccharide 2, monosaccharide 1 is GalNAc only when monosaccharide 2 is Glc, n is 1 to 100, with the proviso that there is always at least one α-fucosyl or α-fucosyl analogous group present in the molecule, and p and k are 0 or 1, and $1 \leq m \leq 1000$, X is a monosaccharide selected from the group consisting of Glc, GlcNAc, Gal or GalNAc, optionally in reduced form, or oligosaccharide containing one or more of said monosaccharide units, the monosaccharide 2 being β1–3 or β1–4 linked to saccharide X, Y is a spacer or linking group capable of linking X to Z, and Z is a mono- or polyvalent carrier molecule.

2. The oligosaccharide according to claim 1, wherein B is α-L-fucosyl.

3. The oligosaccharide according to claim 2, wherein monosaccharide 1 is Glc or GlcNAc.

4. The oligosaccharide according to claim 1, wherein m is 1 to 100, and n is 1 to 10.

5. The oligosaccharide according to claim 4, wherein m is 1 to 10.

6. The oligosaccharide according to claim 1, wherein they have the formula

IA wherein the symbols have the meanings given in connection with the formula I in claim 1, and wherein the monosaccharides 1 and 2 are independently Glc and GlcNAc, B is L-fucosyl, and X is Glc or GlcNAc or a β1–3 or β1–4 linked oligomer comprising up to 10 units of Glc and/or GlcNAc.

7. The oligosaccharide according to claim 1, wherein A is H and the monosaccharides 1 and 2 are independently Glc or GlcNAc, B is L-fucosyl, p and k=0 and n=m=1, and X is Glc or GlcNAc or a β1–3 or β1–4 linked oligomer comprising up to 10 units of Glc and/or GlcNAc having the formula

IB

8. The oligosaccharide according to claim 1 having the formula

Glc/GlcNAcβ1–4(Fucβ1–3)Glc/GlcNAc(β1–4Glc/GlcNAc)$_{n'}$.

wherein n' is the integer 1 to 8.

9. The oligosaccharide according to claim 8, wherein n' is the integer 1 to 6.

10. The oligosaccharide according to claim 1 having the formula

GlcNAcylβ1–4(Fucα1–3(GlcNAc(β1–4GlcNAc)$_{n'}$.

wherein n' is the integer 1 to 8 and acyl is an alkanoyl group which contains 8 to 24 carbon atoms and 1 to 3 double bonds.

11. The oligosaccharide according to claim 1 having the formula

Glcβ1-(-3GalNAc/GlcNAcβ1–4(Fucα1–3/H)Glcβ1-)$_n$-3GalNAcol/GlcNAcol wherein $1 \leq n \leq 1000$.

12. A process for the preparation of an oligosaccharide having the formula

I wherein A is H or a glycosidically β1–3 linked D-glucopyranosyl residue (Glcβ1–3), $R_1$ is OH, $R_2$ is H and $R_3$ is OH, acylamido or —NH-acyl or $R_1$ is H, $R_2$ is OH and $R_3$ is acetamido or —NHCOCH$_3$; B is H, an α-L-fucosyl or an α-L-fucosyl analogue, and $R_4$ is OH, acetamido or —NHCOCH$_3$, the curved line between the saccharide units indicating that the monosaccharide 1 is β1–4 linked to monosaccharide 2 when B is linked to the position 3 of the monosaccharide 2, and the monosaccharide 1 is β1–3 linked to monosaccharide 2 when B is linked to the position 4 of the monosaccharide 2, monosaccharide 1 is GalNAc only when monosaccharide 2 is Glc, n is 1 to 100, with the proviso that there is always at least one α-fucosyl or α-fucosyl analogous group present in the molecule, and i) p and k are 0 and m is 1, in which case X is H, an aglycon residue or a monosaccharide selected from the group consisting of Glc, GlcNAc, Gal or GalNAc, optionally in reduced form, or oligosaccharide containing one or more of said monosaccharide units, the monosaccharide 2 being β1–2, β1–3, β1–4 or β1–6 linked to saccharide X, with the proviso that X is not H when both monosaccharides 1 and 2 are GlcNAc, B is L-fucosyl and n is 1 or ii) p is 1, k is 0 or 1 and $1 \leq m \leq 1000$, in which case X is a straight bond, or a mono- or oligosaccharide as defined under i), Y is a spacer or linking group capable of linking the saccharide 2 or X is Z, and Z is a mono- or polyvalent carrier molecule, said process being characterized in that a compound of the formula I, wherein B is always H, is fucosylated with donor nucleotide sugar containing L-fucose, or an analogue thereof, in the presence of a fucosyl transferase enzyme, and the fucosylated saccharide so prepared is optionally recovered.

13. The process according to claim 12, wherein the fucosyltransferase is mammalian α1–3 or α1–3/4 fucosyltransferase.

14. The process according to claim 12 or 13, wherein a N-acetyl-chitooligosaccharide is used as the starting material.

15. The process according to claims 12 or 13, wherein the donor nucleotide sugar containing L-fucose is GDP-L-fucose.

16. The process according to claim 13, wherein the fucosyltransferase is human α1–3 fucosyltransferase or α1–3/4 fucosyltransferase III–VII, IX or α1–3/α1–3/4 fucosyltransferase of human milk.

17. The process according to any one of claim 12, 13 or 16, wherein it comprises the further step of reacting the product obtained with the formula I with β-N-acetylhexosaminidase.

18. The oligosaccharide of claim 1, wherein monosaccharide 1 is Glc.

19. The oligosaccharide of claim 1, wherein monosaccharide 1 is GlcNAcyl.

20. The oligosaccharide of claim 1, wherein monosaccharide 1 is GalNAc.

21. The oligosaccharide of claim 1, wherein monosaccharide 2 is optionally fucosylated Glc.

22. The oligosaccharide of claim 1, wherein monosaccharide 2 is optionally fucosylated GlcNAc.

23. The process according to claim 12, wherein monosaccharide 1 is Glc.

24. The process according to claim 12, wherein monosaccharide 1 is GlcNAcyl.

25. The process according to claim 12, wherein monosaccharide 1 is GalNAc.

26. The process according to claim 12, wherein monosaccharide 2 is optionally fucosylated Glc.

27. The process according to claim 12, wherein monosaccharide 2 is optionally fucosylated GlcNAc.

* * * * *